(12) United States Patent
Snell

(10) Patent No.: US 7,529,588 B1
(45) Date of Patent: *May 5, 2009

(54) METHOD AND APPARATUS TO BACKUP, UPDATE AND SHARE DATA AMONG IMPLANTABLE CARDIAC STIMULATION DEVICE PROGRAMMERS

(75) Inventor: Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 11/208,053

(22) Filed: Aug. 18, 2005

Related U.S. Application Data

(63) Continuation of application No. 10/016,225, filed on Oct. 19, 2001, now Pat. No. 6,961,617.

(51) Int. Cl.
    *A61N 1/08* (2006.01)
(52) U.S. Cl. .......................... 607/59; 607/60
(58) Field of Classification Search .................. 607/59, 607/60, 32, 31; 705/2, 3; 128/904
    See application file for complete search history.

(56) References Cited

U.S. PATENT DOCUMENTS

| | | | |
|---|---|---|---|
| 4,596,255 A | 6/1986 | Snell et al. ................. 128/697 |
| 4,712,555 A | 12/1987 | Thornander et al. ... 128/419 PG |
| 4,788,980 A | 12/1988 | Mann et al. ........... 128/419 PG |
| 4,791,936 A | 12/1988 | Snell et al. ................. 128/697 |
| 4,940,052 A | 7/1990 | Mann et al. ........... 128/419 PG |
| 4,944,298 A | 7/1990 | Sholder ................. 128/419 PG |
| 5,466,254 A | 11/1995 | Helland ...................... 607/123 |
| 5,716,382 A | 2/1998 | Snell ............................ 607/30 |
| 5,884,323 A | 3/1999 | Hawkins et al. .............. 707/201 |
| 5,974,341 A | 10/1999 | Er et al. ......................... 607/31 |
| 6,000,000 A | 12/1999 | Hawkins et al. .............. 707/201 |
| 6,327,501 B1 | 12/2001 | Levine et al. .................. 607/27 |
| 6,480,743 B1 | 11/2002 | Kirkpatrick et al. ........... 607/45 |
| 6,574,511 B2 | 6/2003 | Lee ............................... 607/60 |
| 2002/0174372 A1* | 11/2002 | Venkataraman ............. 713/400 |

* cited by examiner

Primary Examiner—Kennedy J Schaetzle

(57) ABSTRACT

A system is provided for backing up and synchronizing data stored within a set of programmers used for programming implantable cardiac stimulation devices such as pacemakers or implantable cardioverter defibrillators (ICDs). The data from the programmers that is backed up and synchronized includes programmer software, set up and configuration data, programming parameters, patient personal data, implantable device diagnostic data, and patient diagnostic data received from implanted devices. The implanted devices are classified into one or more groups and the programmer backup system merges and synchronizes data received from all programmers within a particular group. In other words, the backup system operates to ensure that each programmer within a particular group shares the same set up and configuration data, programmer software, patient contact data, and device diagnostic information. Programmers within different groups may have different data stored therein, particularly different set up and configuration data, patient data and the like. The merging and synchronization of data may depend upon the particular type of data. For example, all devices connected to the backup system may be synchronized to have the same programmer software, whereas only programmers within a particular group may be synchronized to have the same set up and configuration data, patient data, and the like.

15 Claims, 7 Drawing Sheets

| PROGRAMMER ID | GROUP ID | DATA |
|---|---|---|
| PROGRAMMER #1 | GROUP #1 | |
| PROGRAMMER #2 | GROUP #1 | |
| PROGRAMMER #3 | GROUP #1 | –PROGRAMMER SOFTWARE<br>–STANDARD SETUP AND CONFIGURATION DATA |
| PROGRAMMER #4 | GROUP #1 | |
| PROGRAMMER #5 | GROUP #1 | |
| ⋮ | ⋮ | |
| PROGRAMMER #1 | GROUP #2 | |
| PROGRAMMER #2 | GROUP #2 | –PROGRAMMER SOFTWARE<br>–STANDARD SETUP AND CONFIGURATION DATA |
| PROGRAMMER #3 | GROUP #2 | |
| ⋮ | ⋮ | |

| PHYSICIAN ID | GROUP ID | DATA |
|---|---|---|
| PHYSICIAN #1 | GROUP #1 | −PREFERRED SETUP AND CONFIGURATION DATA |
| PHYSICIAN #2 | GROUP #1 | −PREFERRED SETUP AND CONFIGURATION DATA |
| PHYSICIAN #3 | GROUP #1 | −PREFERRED SETUP AND CONFIGURATION DATA |
| PHYSICIAN #4 | GROUP #1 | −PREFERRED SETUP AND CONFIGURATION DATA |
| PHYSICIAN #5 | GROUP #1 | −PREFERRED SETUP AND CONFIGURATION DATA |
| ⋮ | ⋮ | ⋮ |
| PHYSICIAN #1 | GROUP #2 | −PREFERRED SETUP AND CONFIGURATION DATA |
| PHYSICIAN #2 | GROUP #2 | −PREFERRED SETUP AND CONFIGURATION DATA |
| PHYSICIAN #3 | GROUP #2 | −PREFERRED SETUP AND CONFIGURATION DATA |
| ⋮ | ⋮ | ⋮ |

| IMPLANTED DEVICE | GROUP ID | DATA |
|---|---|---|
| IMPLANTED DEVICE #1 | GROUP #1 | −PATIENT PERSONAL DATA<br>−DEVICE DIAGNOSTIC DATA<br>−PATIENT DIAGNOSTIC DATA |
| IMPLANTED DEVICE #2 | GROUP #1 | −PATIENT PERSONAL DATA<br>−DEVICE DIAGNOSTIC DATA<br>−PATIENT DIAGNOSTIC DATA |
| IMPLANTED DEVICE #3 | GROUP #1 | −PATIENT PERSONAL DATA<br>−DEVICE DIAGNOSTIC DATA<br>−PATIENT DIAGNOSTIC DATA |
| ⋮ | ⋮ | ⋮ |
| IMPLANTED DEVICE #1 | GROUP #2 | −PATIENT PERSONAL DATA<br>−DEVICE DIAGNOSTIC DATA<br>−PATIENT DIAGNOSTIC DATA |
| IMPLANTED DEVICE #2 | GROUP #2 | −PATIENT PERSONAL DATA<br>−DEVICE DIAGNOSTIC DATA<br>−PATIENT DIAGNOSTIC DATA |
| IMPLANTED DEVICE #3 | GROUP #2 | −PATIENT PERSONAL DATA<br>−DEVICE DIAGNOSTIC DATA<br>−PATIENT DIAGNOSTIC DATA |
| ⋮ | ⋮ | ⋮ |

METHOD AND APPARATUS TO BACKUP, UPDATE AND SHARE DATA AMONG IMPLANTABLE CARDIAC STIMULATION DEVICE PROGRAMMERS

CROSS-REFERENCE TO RELATED APPLICATIONS

This application is a continuation of copending U.S. patent application Ser. No. 10/016,225, filed Oct. 19, 2001.

FIELD OF THE INVENTION

The invention generally relates to programmers for use with implantable cardiac stimulation devices and in particular to techniques for backing up, updating and sharing data among groups of programmers.

BACKGROUND OF THE INVENTION

Implantable cardiac stimulation devices, particularly pacemakers and implantable cardioverter defibrillator (ICDs), are often configured to be used in conjunction with a programmer which allows a physician to program the operation of the implanted device to, for example, control the specific parameters by which the implanted device detects an arrhythmia and responds thereto. For instance, the programmer may allow the physician to specify the sensitivity with which the implanted device senses electrical signals within the heart and to further specify the amount of electrical energy to be employed for pacing the heart in circumstances where expected heart signals are not sensed. Current state of the art programmers permit dozens or hundreds of device control parameters to be individually programmed to thereby permit the operation of an implanted device to be tailored to the needs of the particular patient to provide optimal functionality while minimizing the risk of any unnecessary therapy. Additionally, the programmer may be configured to receive and display a wide variety of diagnostic information detected and recorded by the implanted device, such as internal electrocardiogram (IEGM) recordings or histograms of paced vs. sensed electrical events in the heart. The programmer may further operate to analyze the data received from the implanted device to assist the physician in rendering a diagnosis as to any possible arrhythmias and to assist the physician in programming the implanted device to provide appropriate therapy.

To provide these many functions, state of the art programmers typically employ fairly complicated software, and the specific functions to be performed by a given programmer and the manner in which the functions are performed may vary from programmer to programmer depending upon the software installed therein. For example, the manner by which diagnostic data is displayed and the manner by which programming commands are entered may differ from one programmer to another depending upon the version of the programmer software. Preferably, all programmers at a particular hospital or clinic are maintained so as to share the same software such that each physician using any one of the programmers can quickly, easily and reliably program implanted devices for his or her patients. It is possible, however, that the programmers may not be properly maintained and hence may not share the same programmer software. As a result of differences in the software, there is a risk that a physician might misinterpret diagnostic data displayed by the programmer and might incorrectly program an implanted device.

Accordingly, it would be highly desirable to provide techniques for ensuring that all programmers within a group of programmers share the same programmer software, such as all programmers within a particular hospital or clinic. It is to this end that aspects of the invention are directed.

After an implanted device has been initially programmed, the patient typically must return to their physician a number of times for follow-up sessions to permit the physician to verify that the implanted device is functioning properly and to re-program the device if needed. During each re-programming session, a considerable amount of data may need to be retrieved from the implanted device by the programmer, such as IEGM recordings, histograms of sensed vs. paced events and the like. Preferably, the data is stored by the programmer so that the physician can quickly and easily review the stored data in combination with any new data whenever the implanted device needs to be reprogrammed. However, in some cases, the follow-up session must be performed using a different programmer because the original programmer is no longer in use or because the original programmer is currently being used by another physician. In other cases, the follow-up session is performed by the physician at a different location such as at a hospital rather than at the office of the physician, and hence a different programmer must be used. In still other cases, the follow-up session is performed by a different physician having access to an entirely different set of programmers. As can be appreciated, with physicians potentially using multiple programmers at different locations and with patients potentially visiting multiple physicians, it is not often possible for stored data from previous programming sessions to be reviewed by the physician, possibly resulting in less than optimal re-programming of the implanted device. Still other problems arise if an individual programmer fails, and all patient data stored therein is lost.

Accordingly, it would be highly desirable to provide improved techniques for backing up and sharing data among programmers and it is to this end that aspects of the invention are directed as well.

SUMMARY OF THE INVENTION

In accordance with the invention, a programmer backup system is provided for backing up and synchronizing data stored within a plurality of implantable cardiac stimulation device programmers.

In an exemplary implementation of the invention, the implantable cardiac stimulation devices are pacemakers or ICDs. The programmers are dedicated implantable cardiac stimulation device programmers or are personal computers (PCs) provided with software and hardware for performing cardiac stimulation device programming. The data to be backed up and synchronized includes programmer software, standard programmer setup and configuration data, physician preferences for setup and configuration data, programming parameters for individual implanted devices, patient personal data including medical histories, implantable device diagnostic data, and patient diagnostic data. The programmer backup system is configured to control the synchronization of data among programmers depending upon whether the programmers are within a common group of programmers. To this end, the backup system operates to ensure that each programmer within a particular group shares the same data, while permitting programmers of different groups to share different data. In this manner, all programmers within a particular hospital or clinic may share the same data whereas programmers at different hospitals or clinics may share different data. The synchronization of data among groups of programmers may further depend upon the particular type of data. For example, all programmers connected to the backup system may be synchronized to share the same programmer software, whereas only programmers within a common group are synchronized to share the same patient data. The backup system is configured either to provide programmer access to the synchronized data so that individual programmers can download specific data on-demand or is configured to transmit synchronized data to the programmers for storage therein so that each programmer maintains an up-to-date version of the database. Whether the data is maintained at the backup system or is transmitted to the individual programmers depends on the type of data. Programmer software and programmer setup and configuration data is preferably transmitted to all programmers for storage therein. Patient-specific data such as medical histories and the like are preferably transmitted to individual programmers only on-demand.

Also in the exemplary implementation, all data to be backed up and synchronized by the backup system is time stamped. The backup system merges data received from all programmers within a particular group by examining the time stamps then using the most recent data to supercede any preceding data. The merging of data is performed either automatically or only subsequent to user review. To this end, means are provided for displaying all data, for flagging inconsistencies in the data, and for inputting and processing commands for retaining, editing and discarding individual items. The means for displaying the data may include, for example, browser software for accessing the data of the backup system via the Internet, local area network (LAN), wide area network (WAN), or other suitable computer network. In the alternative, at least one of the programmers is provided with means for displaying and modifying data stored within the backup system such that a separate browser is not required. In any case, once data received from all programmers within a particular group has been merged, the merged data is transmitted to the programmers of the group to thereby synchronize the programmers of the group. Also, depending upon the implementation, the merging of data is performed either periodically, on demand, or substantially continuously.

By providing a system for backing up and synchronizing data among programmers, a physician using any of the programmers within the same group is thereby assured that each will have the same patient data and programmer software. Likewise, if a particular patient has a follow-up session with a different physician, that physician can easily access data for the particular patient, assuming that the programmer employed by the physician is within the same group of programmers used in a preceding programming session. Also, by backing up and synchronizing data among an entire group of programmers, if any particular programmer malfunctions, the data stored therein is easily accessed using another programmer within the group. Indeed, even if all programmers within a particular group malfunction, the data can be retrieved from the backup system for use with a new set of programmers.

Method and apparatus implementations of the invention are provided. Other objects, features, and advantages of the invention are provided as well.

BRIEF DESCRIPTION OF THE DRAWINGS

Further features and advantages of the invention may be more readily understood by reference to the following description taken in conjunction with the accompanying drawings, in which:

FIG. 5 is illustrates a database of the backup system of FIG. 4 for storing programmer data; and FIG. 6 is illustrates a database of the backup system of FIG. 4 for storing physician preferences;

FIG. 7 is illustrates a database of the backup system of FIG. 4 for storing implanted device data and patient data.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the exemplary embodiments of the invention that follows, like numerals or reference designators will be used to refer to like parts or elements throughout.

Figure 1:
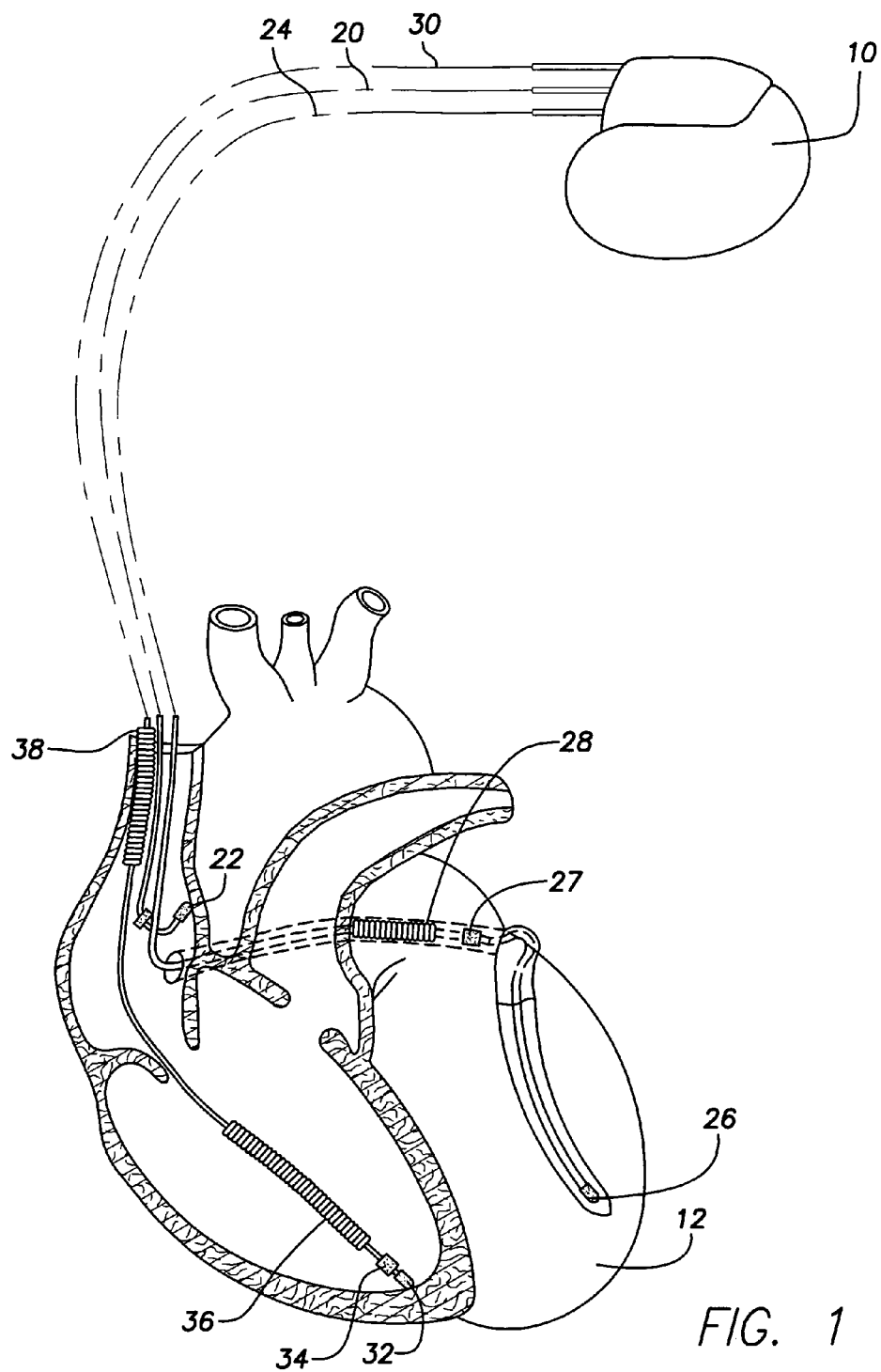
FIG. 1 is a simplified diagram illustrating an implantable stimulation device in electrical communication with at least three leads implanted into a patient's heart for delivering multi-chamber stimulation and shock therapy.
Figure 2:
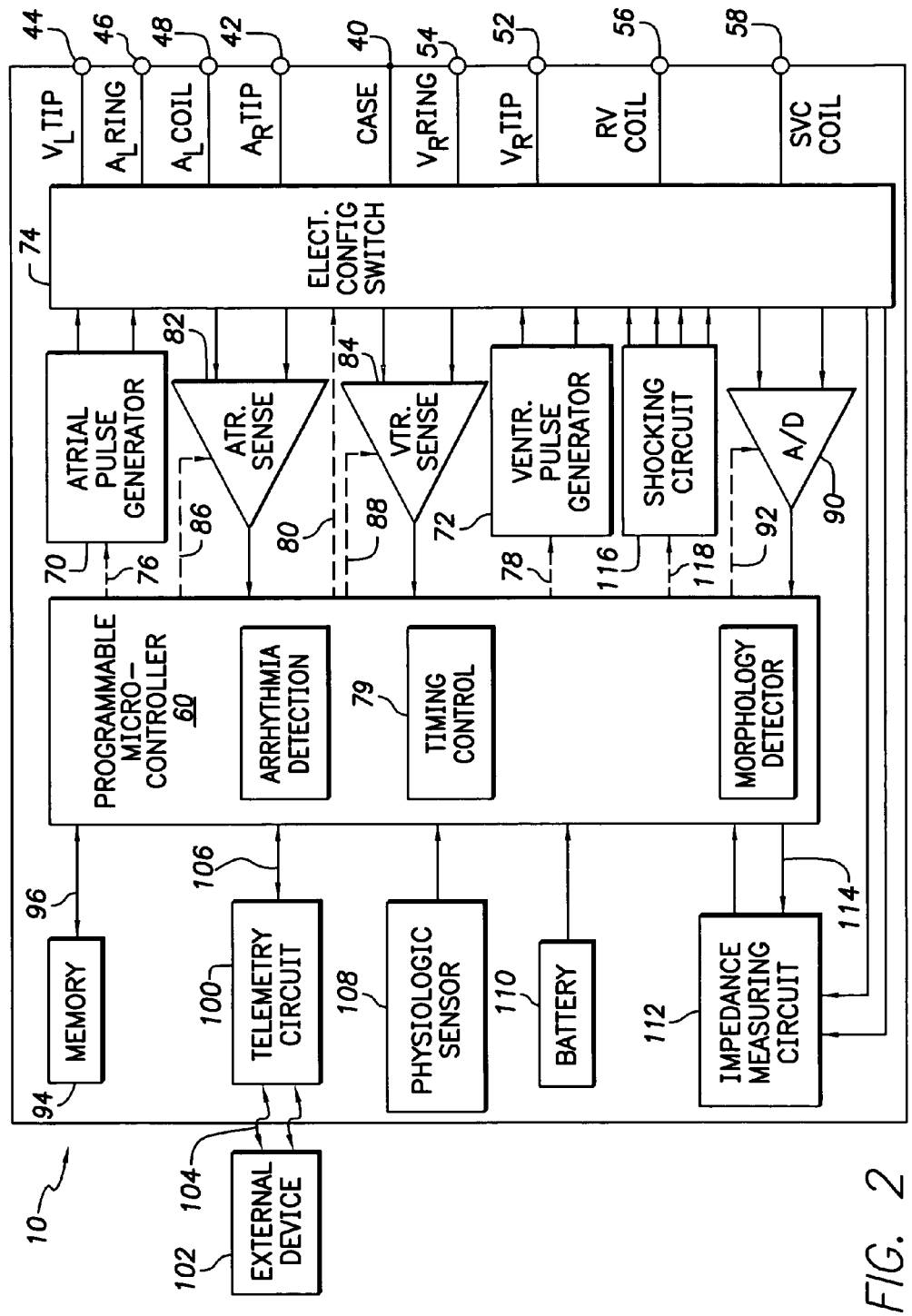
FIG. 2 is a functional block diagram of a multi-chamber implantable stimulation device illustrating the basic elements of a stimulation device, which can provide cardioversion, defibrillation and pacing stimulation in four chambers of the heart.
Figure 3:
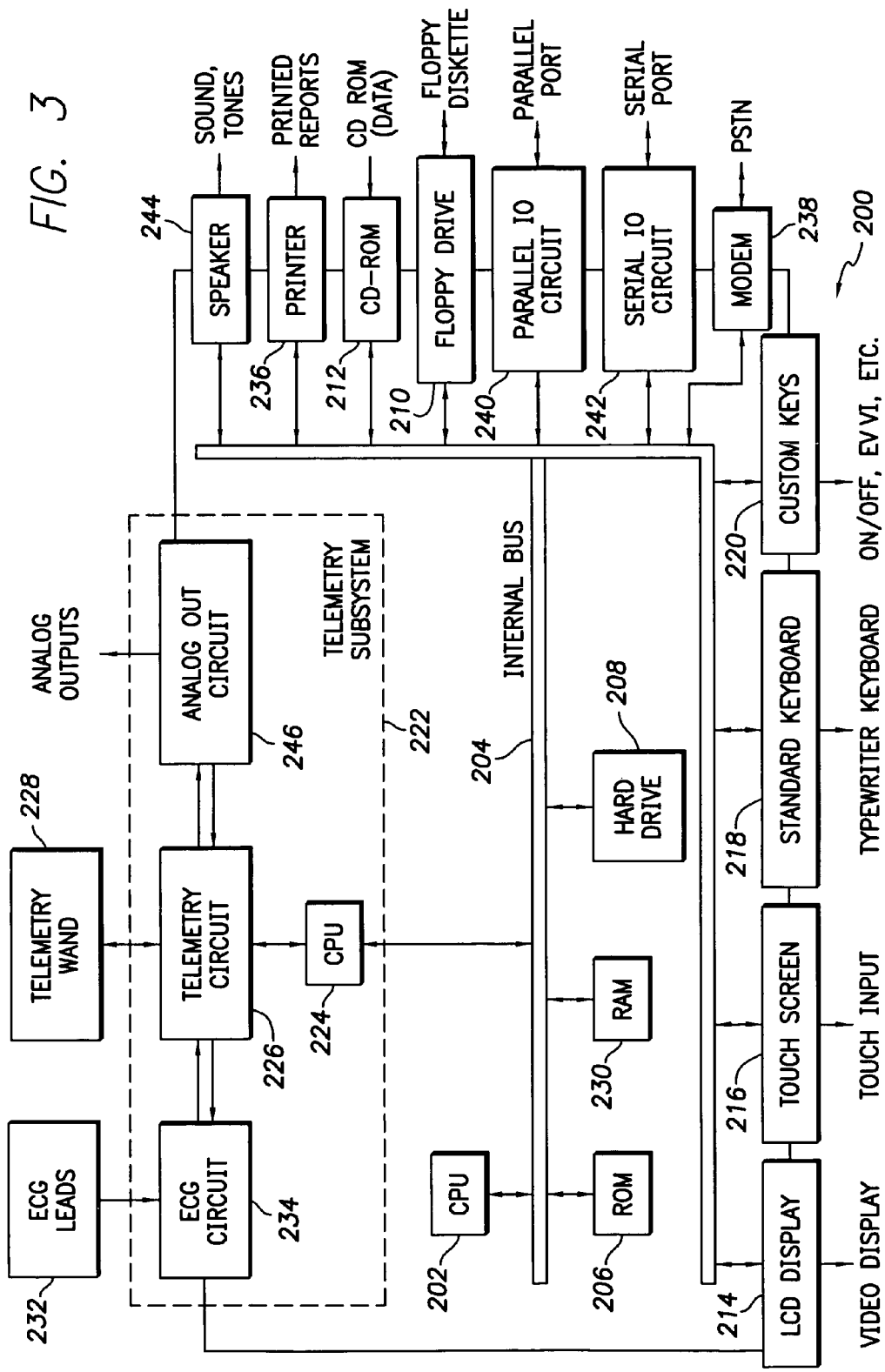
FIG. 3 is a functional block diagram illustrating components of a programmer for use in programming the implantable device of FIG. 1.

Initially, with reference to FIGS. 1-3, an overview of an exemplary implantable device and an exemplary device programmer are provided. Then a detailed description of the backup and synchronization system for use with implantable devices and device programmers is provided with reference to FIGS. 4-7.

Implantable Stimulation Device

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

Representative types of control circuitry that may be used with the invention or modified for use with the invention include the microprocessor-based control system of U.S. Pat. No. 4,940,052 (Mann et al.), the state-machine of U.S. Pat. Nos. 4,712,555 (Thornander et al.) and 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time. See U.S. Pat. Nos. 4,596,255 and 4,791,936, by Snell et al., both entitled "Apparatus for Interpreting and Displaying Cardiac Events of a Heart Connected to a Cardiac Pacing Means."

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted medical device may be found in U.S. Pat. No. 5,716,382 entitled "Programmer for an Implantable Cardiac Stimulating Device." Prior to reprogramming specific parameters, the physician may control the external programmer to display any or all of the data retrieved from the implanted device or from the ECG leads, including displays of ECGs, IEGMs, and statistical patient information. Further information pertaining to the types of information which may be displayed using programmer may be found in U.S. Pat. No. 5,974,341 entitled "Method and Apparatus for Detecting and Displaying Diagnostic Information in Conjunction with Intracardiac Electrograms and Surface Electrocardiograms." Any or all of the information displayed by programmer may also be printed using a printer 236.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports may be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

Figure 4:
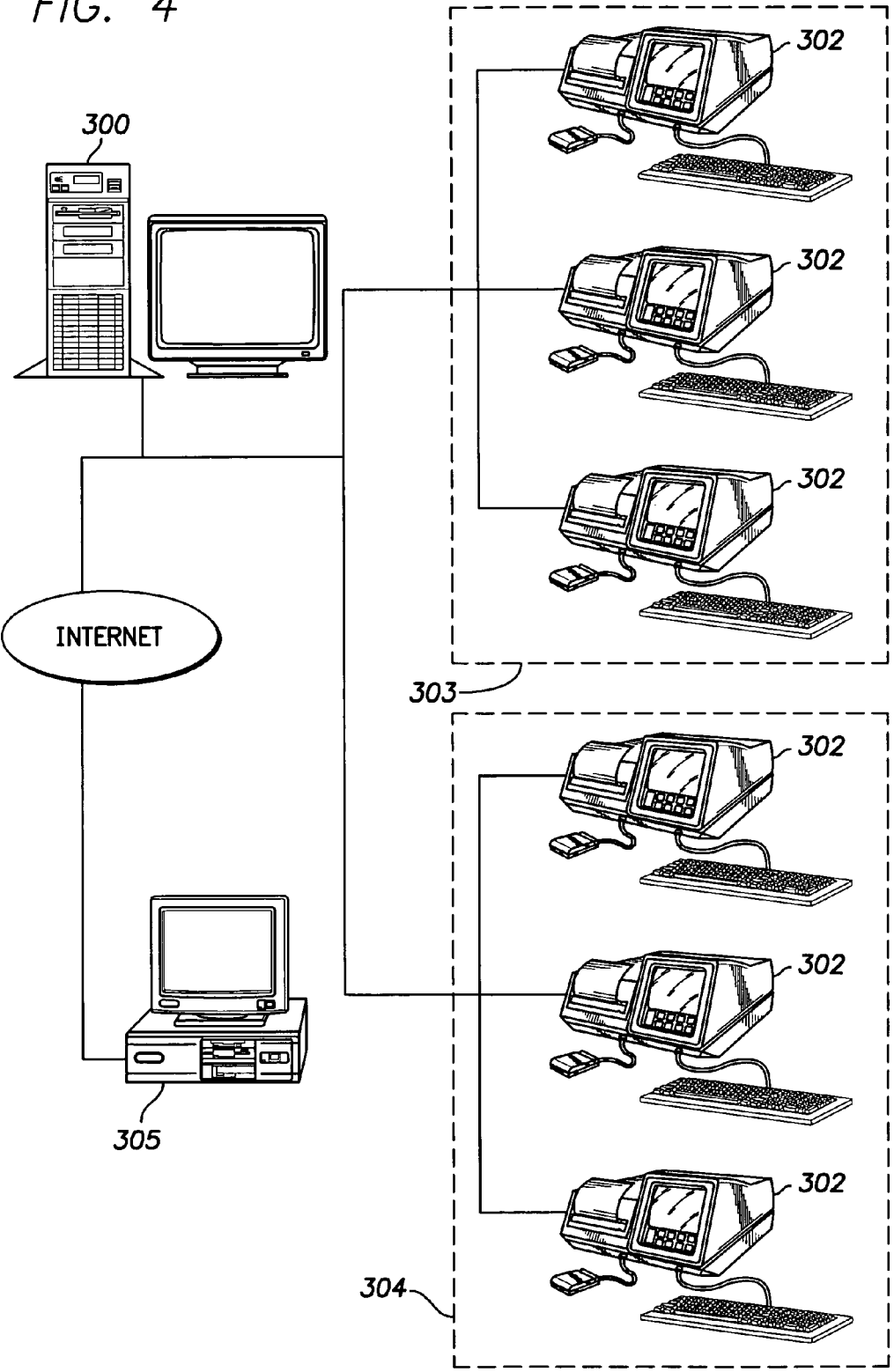
FIG. 4 is a block diagram providing an overview of a programmer backup system, configured in accordance with an exemplary embodiment of the invention, for backing up data stored within a set of programmers such as those illustrated in FIG. 3.

FIG. 4 illustrates a system for synchronizing and backing-up a network of programmers such as the programmer of FIG. 3. A central backup system 300 is provided for use with a distributed network of programmers 302 installed within hospitals, clinics, or patient homes. Each programmer is preferably a full-function programming unit capable of programming all functions of an implanted cardiac stimulation device and capable of displaying diagnostic information received from the implanted device. Each programmer may be a dedicated programmer unit having internal components as illustrated in FIG. 3 or may be a personal computer (PC) provided with necessary software and hardware for performing implanted device-programming functions. In the specific implementation of FIG. 4, the central backup system communicates with the programmers via the PSTN or via other land line communication link, such as T1 line, ISDN line, or the like. Alternatively, individual programmers may be provided with wireless communication devices to permit the central backup system to communicate with the programmers via satellite based wireless communication systems, cellular telephone systems, or the like. In still other implementations, the individual programmers communicate with the central backup system via the Internet or other interconnected computer network.

Backup system 300 operates to backup data stored within any of the programmers within an internal data storage system. The various programmers are logically arranged within groups, with the data from various programmers within the same group stored using a group ID within the backup storage system. In FIG. 4, only two such groups of programmers 303 and 304 are shown, each having three individual programmers, but typically many more groups of programmers are connected to the backup system, each having many individual programmers. In many cases, the programmers of a particular group are located at a single location, such as a hospital or clinic and are used by a group of physicians associated with the hospital or clinic. However, all programmers within a single group need not be located at a single location. For example, all programmers operated by a commonly-owned network of hospitals may be designated as being within the same group even though the programmers are installed within widely separated hospitals. As another example, a group of programmers installed at various remote medical clinics may be designated as being within the same group.

In addition to backing up all data within all programmers connected to the system, the backup system also serves to synchronize data among programmers of the same group, in accordance with the programming of the system. By "synchronizing" data, it is meant that the backup system periodically ensures that all programmers being synchronized are updated to store or have access to the same data. Several different types of data are stored, with some of the types of data being synchronized and other types not being synchronized. In one example, all programmers connected to the backup system are synchronized to have the same programmer software, whereas only programmers within a particular group are synchronized to share common setup and configuration data, patient data, and the like. All data to be backed up and synchronized by the backup system is time stamped by the backup system. The backup system merges data received from all programmers within a particular group by examining the time stamps of the data, then using the most recent data to supercede any inconsistent preceding data. Depending upon the programming of the overall system, merging of data is performed either automatically or only subsequent to a user review. To this end, a browser 305 is interconnected via the Internet and World Wide Web to the backup system to permit a user to access and examine any of the data within the backup system. Software operating within the browser or within the backup system identifies and displays any inconsistent data, then receives commands from the user for resolving any inconsistencies. For example, if the backup system detects that data for two separate patients specifies the same implanted device ID number, then this inconsistency is displayed via the browser to alert the user. In other examples, rather than accessing stored data via the Internet, the browser may access the data via a LAN, WAN, or other suitable computer network. In one specific example, the sales representative or field clinical engineer reviews and updates programmer software from a browser connected to the system via the Internet. Any updates provided by the sales representative or field clinical engineer are then automatically propagated to all programmers connected to the system or to all programmers within a particular group. Rather than providing a separate browser for accessing and modifying data to be merged, one or more of the individual programmers may be provided with that capability or the backup system itself may be provided with that capability.

In any case, once data received from all programmers within a particular group has been successfully merged, the merged data is then available to the programmers of the group. Depending upon the programming of the system and on the amount of memory available within each individual programmer, the merged data is either transmitted to each individual programmer for storage therein or is merely made available to the programmers such that the programmers can access the data when needed. If the merged data is to be transmitted to the programmers, the transmission of the merged data is performed either periodically, on demand, or substantially continuously. To permit transmission of merged data to be performed substantially continuously, the individual programmers should be continuously connected to the backup system via a T1 link or other high-speed connection. For programmers connected to the backup system via a dial-up modem, merged data may be transmitted whenever the programmer is in dialup communication with the backup system. Details regarding techniques for synchronizing data among multiple computer systems may be found in U.S. Pat. No. 6,000,000 to Jeffrey Hawkins and Michael Albanese (which is incorporated by reference herein) and such techniques may be employed with the present invention.

With reference to FIGS. 5-7, particular types of data processed by the backup system will now be described. The backup system has a first database 306 for storing programmer data for use by individual programmers, as shown in FIG. 5; a second database 308 for storing preferences for setup and configuration data for individual physicians, as shown in FIG. 6; and a third database 310 for storing implanted device data for individual implanted devices, as shown in FIG. 7.

The programmer data of database 306 of FIG. 5 includes programmer software and standard programmer setup and configuration data. The programmer software is the software which actually controls the programmer to, for example, retrieve and display diagnostic data from an implanted device, input programming commands from a physician, and transmit the programming commands to the implanted device for programming the implanted device. For programmers configured as general-purpose computers modified to program implanted devices, the programmer software typically operates under the general control of an operating system software such as Windows™. For programmers configured as dedicated hardware devices, no separate operating system may be required. The standard programmer setup and configuration data controls the operation of the programmer software. For example, the standard setup and configuration data may specify the manner by which routine follow-ups are performed and may further specify particular fonts, point sizes, and display colors for use by the programmer software. The standard programmer setup and configuration data may further specify whether any shortcut commands are to be enabled and, if so, may store specific shortcut commands to be associated with various functions of the software of the programmer. The standard programmer setup and configuration data represents the default setup and configuration data for all programmers of a particular group. The data of database 306 is arranged by group with each programmer in the group assigned a unique programmer ID. Generally, a programmer is assigned to only one group. Hence, programmer #1 of group #1 is a different programmer than programmer #1 of group #2.

The backup system is configured to ensure that the programmer data of database 306 is synchronized to be the same for all programmers within a particular group, though the programmer data may differ from group to group. However, the backup system also stores physician preferences for the setup and configuration data to permit individual physicians to quickly customize the operation of a programmer. To this end, as shown in FIG. 6, database 308 stores preferences for the setup and configuration data for various physicians along with corresponding unique physician IDs. As with database 306, the data of database 308 is arranged by group with each physician assigned a unique physician ID within the group. Generally, a physician only uses the programmers of one group. Hence, physician #1 of group #1 is a different physician than physician #1 of group #2.

Referring now to FIG. 7, database 310 of the backup system stores implanted device data, programming parameters for particular implanted devices, patient personal data and patient diagnostic data. The implanted device data includes diagnostic information transferred from an implanted device to one of the programmers specifying the operation of the implanted device. Examples include information pertaining to battery RRT, lead impedances, battery voltage, and information identifying the particular implanted device, such as its manufacturer, serial number, product number and the like. The programming parameters include that latest set of parameters used to program the implanted device and specify, for example, the mode of operation of the device (such as VVI or DDI), the sensitivity for detecting electrical signals in the heart, and the voltage used for pacing pulses or defibrillation shocks. The patient personal data includes patient medical histories, patient contact information, and the like for each patient who has had an implanted device programmed using any of the programmers connected to the backup system. The patient diagnostic data includes any patient information transmitted from an implanted device to one of the programmers such as IEGM data, average heart rate, as well as statistical information pertaining to the heart activity of the patient.

Examples of patient diagnostic data are described in U.S. Pat. No. 5,974,341 to Er et al., which is incorporated by reference herein. As with the other databases, database 310 is arranged by group with each implanted device of a particular group assigned a unique implanted device ID. Generally, the implanted device of a patient is only programmed by a physician using programmers of one particular group of programmers. Hence, implanted device #1 of group #1 is a different implanted device than implanted device #1 of group #2.

Thus a wide variety of data is stored in the databases of FIGS. 5-7. As noted above, the backup system is configured either to provide programmer access to the synchronized data so that individual programmers can download specific data on-demand or is configured to frequently transmit synchronized data to the programmers for storage therein so that each programmer maintains an up-to-date version of the database. Whether the data is maintained at the backup system or is transmitted to the individual programmers can depend on the type of data, with frequently-used data, such as the programmer software and programmer setup and configuration data, preferably being periodically transmitted to all programmers for storage therein and with less frequently-used data, such as patient-specific data, preferably being transmitted to an individual programmers only on-demand.

The manner by which the backup system uses the shared databases will now be described with further reference to FIG. 4. In the following example, each individual programmer of each group maintains a copy of the programmer data for their respective group in their internal database and accesses all other data on-demand from the backup system. It is assumed that the latest versions of the programmer data, including both the programmer software and the standard setup and configuration data, have already been transferred to each programmer of each group and stored therein. Upon initiating a programming session with a patient using one of the programmers, the physician first enters his or her unique physician ID into the programmer. The physician ID and a pre-stored group ID are transmitted to the backup system, which retrieves any preferred setup and configuration data for the physician stored within database 308 (FIG. 5) and transmits the data to the programmer so that the programmer may be configured using the setup and configuration data preferred by the physician for the duration of the programming session. Hence, the physician can efficiently operate the programmer by, for example, exploiting any shortcut commands that he or she has enabled. By providing uniformity among programmers for a given physician, the risk of programming errors is reduced. Also, the overall time required by the physician to program the operation of an implanted device may be reduced because the physician will be familiar with the programmer software and the programming commands. If the physician has not entered his or her physician ID or has not previously stored preferences for the setup and configuration data, then the standard setup and configuration data already stored in the programmer is used instead. Additionally or in the alternative, the system may provide for a remote set-up via a browser, an off-line set up, or a scheduled set-up. The system may also provide for the set-up of individual physician/patient lists.

Once the programmer has been configured to the physician preferences, the programmer retrieves data from the implanted device within the patient. The data retrieved from the implanted device includes the ID of the implanted device, the current set of programming parameters used by the implanted device, any patient diagnostic data stored therein, such as IEGM data, paced vs. sensed event histogram data, and any device diagnostic data, such as lead impedance data, RRT data, and the like. Under the control of the physician, the programmer generates various displays of the information retrieved from the implanted device. The retrieved data, the implanted device ID and the group ID are transmitted to the backup system for storage of the retrieved data within database 310 (FIG. 5). The backup system also retrieves any previous programming parameters, patient personal data, device diagnostic data and patient diagnostic data already stored within database 310 for the implanted device and transmits the data to the programmer so that the physician can also access and display the previously stored data along with any new data. Hence, for example, the physician can compare IEGM data just retrieved from the implanted device with IEGM data stored in the backup system from a previous programming session.

Following review by the physician of data retrieved from the backup system, new data retrieved from the implanted device and from direct observation of the patient, the physician may choose to reprogram various parameters of the implanted device to, for example, improve the performance of the device, adjust for new medications taken by the patient, or to address any new conditions developed by the patient. If so, the new programming parameters are transmitted to the implanted device and are also transmitted to the backup system so that the backup system can stored the latest set of programming parameters for the device. The physician also updates the patient medical history and the programmer transmits the updates to the medical history to the backup system for storage therein. The physician may also update his or her own preferences to the setup and configuration data.

Eventually, the patient may return for a follow-up session performed by a different physician using a different programmer of the same group. Upon initiating the follow-up session with the patient, the physician of the follow-up session enters his or her unique physician ID into the programmer and the programmer is automatically configured using any preferred setup and configuration data for the physician stored within the backup session. The programmer retrieves data from the implanted device and, using the device ID, also retrieves data for the patient stored in the backup system. The physician of the follow-up session may then choose to reprogram various parameters of the implanted device and, if so, the new programming parameters are transmitted both to the implanted device and to the backup system. The physician of the follow-up session updates the patient medical history, and the updates are in turn transmitted to the backup system for storage therein.

Whenever the backup system receives data from a programmer, the backup system compares the data with data already stored therein and merges the new data with the previously stored data as needed. In this regard, all data transmitted to the backup system is time-stamped permitting older data to be over-written by new data. Whether older data is overwritten by newer data or merely supplemented with the newer data depends on the particular type of data, the programming of the backup system and the amount of memory available in the backup system. In one example, the backup system is programmed to overwrite old physician preference data with new preference data and to supplement stored implanted device programming parameters with new programming parameters. In this manner, a physician can retrieve and display the complete history of the programming an implanted device of a patient to ensure that the device is not merely being reprogrammed to a previous set of programming parameters already found to be non-optimal.

Thus, regardless of which physician is programming an implanted device and regardless of which programmer is being used to perform the re-programming, the physician has easy access to the same programming parameters, patient personal information, patient diagnostic information, and implanted device diagnostic information. Preferably, the entire medical history for the patient is stored in the backup system so that the physician has immediate access to the medical history without the need to consult any additional sources. Easy access to the medical history ensures that any pertinent information contained therein is readily accessible by the physician to help ensure efficient and reliable programming of the implanted device to meet patient needs. This is particularly important in the event either the physician or the patient travels among widely spaced locations. As one specific example, if a patient spends a portion of the year in one geographical location and another portion of the year in another, a physician who needs to reprogram the implanted device of the patient can gain easy access to all pertinent medical information for the patient via the local programmer. Likewise, for physicians who use programmers at widely scattered locations, such as at remote medical clinics, the physician can reliably access his or her preferred setup and configuration information. Also, by backing up data among an entire group of programmers, if any particular programmer malfunctions, no data is lost. Indeed, even if all programmers malfunction, data can be retrieved from the backup system for use with new programmers.

The use of the backup system also facilitates software upgrades to the programmers as well. For example, a new version of programmer software may be loaded into browser 305 (FIG. 4) for transmission to the backup system then downloaded to all other programmers within for immediate use. In this manner, the programmer software is synchronized among all programmers or at least among groups of programmers. By synchronizing the programming software, a physician using any one of the programmers is thereby assured that the same programmer software is running, thereby minimizing the risk of programming errors caused by differences in programmer software versions. The programmer software may be organized as multiple modules to facilitate more efficient updating by allowing updates of only those portions of the software that has changed. New versions of programmer data may alternatively be loaded directly via the backup system computer or via any of the individual programmers, assuming permission for such actions has been granted.

What has been described are various backup and synchronization systems for use with implantable cardiac stimulation devices. The various functional components of the exemplary systems may be implemented using any appropriate technology including, for example, microprocessors running software programs or ASICs executing hard-wired logic operations. The exemplary embodiments of the invention described herein are merely illustrative of the invention and should not be construed as limiting the scope of the invention.

What is claimed is:

1. A backup and synchronization system for use with a plurality of programmers for programming implantable cardiac stimulation devices, the system comprising:
   means for receiving information from the programmers;
   means for backing up the information received from the programmers;
   means for synchronizing the information received from the programmers; and
   means for selectively transmitting synchronized information to the programmers.

2. The backup and synchronization system for of claim 1 wherein the means for synchronizing information received from the programmers operates to automatically merge information received from different programmers, with the information merged so that recent information supercedes older information.

3. The backup and synchronization system of claim 2 wherein the means for synchronizing information detects any inconsistent information received from the programmers that cannot be merged automatically.

4. The backup and synchronization system of claim 2 further comprising browser means, connected to the backup system through the Internet, for displaying and modifying information stored within a means for storing of the means for synchronizing information.

5. The backup and synchronization system of claim 2 wherein the plurality of programmers are classified into one or more groups and wherein the means for synchronizing operates to synchronize information only among programmers within a particular group.

6. The backup and synchronization system of claim 2 wherein the information to be synchronized is classified into one or more types of information and wherein the means for synchronizing operates to synchronize only selected types of information stored within the programmers.

7. The backup and synchronization system of claim 2 wherein the means for synchronizing operates to synchronize one or more of programmer software data, programmer setup and configuration data, physician preferences for setup and configuration data, programming parameters, patient personal data, implantable device diagnostic data, and patient diagnostic data stored within the programmers.

8. The backup and synchronization system of claim 2 wherein the means for synchronizing operates to synchronize information periodically, on-demand, or substantially continuously.

9. A system for use with a plurality of programmers for programming implantable cardiac stimulation devices, the system comprising:

a central computer adapted to communicate with the plurality of programmers and to receive information from the programmers, wherein the central computer is operative to synchronize the information received from the programmers, and further operative to transmit the synchronized information to the plurality of programmers.

10. The system for of claim 9 wherein the central computer is operative to merge information received from different programmers, with the information merged so that recent information supersedes older information.

11. The system of claim 10 further comprising a display to display information stored by the central computer.

12. The system of claim 9 wherein the plurality of programmers are classified into one or more groups and wherein the central computer is operative to synchronize information only among programmers within a particular group.

13. The system of claim 9 wherein the information to be synchronized is classified into one or more types of information and wherein the central computer is operative to synchronize only selected types of information stored within the programmers.

14. The system of claim 9 wherein the central computer is operative to synchronize one or more of programmer software data, programmer setup and configuration data, physician preferences for setup and configuration data, programming parameters, patient personal data, implantable device diagnostic data, and patient diagnostic data stored within the programmers.

15. The system of claim 9 wherein the central computer is operative to synchronize information periodically, on-demand, or substantially continuously.

* * * * *